(12) United States Patent
Sabo et al.

(10) Patent No.: US 9,522,690 B2
(45) Date of Patent: Dec. 20, 2016

(54) EQUIPMENT TROLLEY

(71) Applicant: Karl Storz GmbH & Co. KG, Tuttlingen (DE)

(72) Inventors: Alexander Sabo, Tuttlingen (DE); Andreas Jansche, Zimmern ob Rottweil (DE); Anika Guempel, Bodmann-Ludwigshafen (DE); Wolfgang Mueller-Beiter, Sigmaringendorf (DE); Rainer Schairer, Albstadt (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 0 days.

(21) Appl. No.: 14/622,268

(22) Filed: Feb. 13, 2015

(65) Prior Publication Data
US 2015/0232113 A1    Aug. 20, 2015

(30) Foreign Application Priority Data

Feb. 18, 2014 (DE) .................. 10 2014 101 997

(51) Int. Cl.
*B62B 5/00* (2006.01)
*B62B 3/02* (2006.01)
*B62B 3/00* (2006.01)
*B62B 3/10* (2006.01)
(Continued)

(52) U.S. Cl.
CPC ................. *B62B 3/02* (2013.01); *A61B 50/10* (2016.02); *A61B 50/13* (2016.02); *B25H 3/00* (2013.01); *B62B 3/002* (2013.01); *B62B 3/10* (2013.01); *A47B 31/00* (2013.01)

(58) Field of Classification Search
CPC .............. B62B 3/02; B62B 3/10; B62B 3/002; B62B 3/00; B62B 3/005; B62B 3/18; B62B 2202/56; B62B 2202/67; B62B 2202/61; A61B 19/0248; A61B 2019/025; A61B 2019/0249; A61B 2019/0256
See application file for complete search history.

(56) References Cited

U.S. PATENT DOCUMENTS 2,973,233 A    2/1961  McPhee
4,045,104 A *  8/1977  Peterson ................... 312/265.4
4,298,099 A *  11/1981 Isaacs ............................ 186/58
(Continued)

FOREIGN PATENT DOCUMENTS

DE    1825620 U    1/1961
DE    9418224 U1   12/1994
(Continued)

OTHER PUBLICATIONS

European Search Report Application No. EP 15 15 5080 Completed: Jul. 9, 2015. Mailing Date: Jul. 17, 2015 7 pages.

*Primary Examiner* — James M Dolak
(74) *Attorney, Agent, or Firm* — Whitmyer IP Group LLC

(57) ABSTRACT

An equipment carrier includes a surface module with a first securing device and a column module with a second securing device. The first securing device on the surface module and the second securing device on the column module are designed corresponding to each other such that the column module and the surface module can be connected to each other with a first, linear movement and a subsequent second, rotational movement of the column module relative to the surface module.

8 Claims, 6 Drawing Sheets

(51) Int. Cl.
*B25H 3/00* (2006.01)
*A47B 31/00* (2006.01)

(56) References Cited

U.S. PATENT DOCUMENTS

| | | | | |
|---|---|---|---|---|
| 4,595,107 | A * | 6/1986 | Welsch | 211/187 |
| 4,620,637 | A * | 11/1986 | Karashima | 211/188 |
| 4,743,040 | A | 5/1988 | Breveglieri | |
| 4,998,023 | A * | 3/1991 | Kitts | 280/47.35 |
| 5,011,240 | A * | 4/1991 | Kelley et al. | 312/249.12 |
| 5,605,344 | A * | 2/1997 | Insalaco et al. | 280/47.34 |
| 6,086,073 | A * | 7/2000 | Tisbo et al. | 280/47.26 |
| 6,478,169 | B2 * | 11/2002 | Krusell | 211/85.7 |
| 6,767,019 | B2 * | 7/2004 | van Hekken | B62B 3/006 108/147.12 |
| 6,796,565 | B2 * | 9/2004 | Choi et al. | 280/47.35 |
| 7,017,603 | B1 * | 3/2006 | Rosine et al. | 137/355.12 |
| 8,720,913 | B2 * | 5/2014 | Fallon et al. | 280/47.35 |
| 9,216,753 | B2 * | 12/2015 | Bryan | B62B 3/02 |
| 9,227,645 | B2 * | 1/2016 | Franco | B60K 7/0007 |
| 9,266,547 | B2 * | 2/2016 | Schumaker | B62B 3/005 |
| 9,272,722 | B2 * | 3/2016 | Dufoure | B25H 1/14 |
| 9,296,405 | B2 * | 3/2016 | Lenkman | B62B 3/02 |
| 9,296,406 | B2 * | 3/2016 | Presley | B62B 3/108 |

FOREIGN PATENT DOCUMENTS

| | | |
|---|---|---|
| DE | 202004001147 U1 | 6/2005 |
| DE | 202006006146 U1 | 10/2006 |
| DE | 202007013817 U1 | 2/2008 |
| DE | 102008054055 A1 | 5/2009 |
| FR | 1200640 A | 12/1959 |
| WO | 2012081016 A1 | 6/2012 |

* cited by examiner ic carrier, in
particular an equipment carrier that can be dismantled,
modified and correctly assembled even by persons not
technically trained, the equipment carrier being in particular
an equipment trolley.

BACKGROUND OF THE INVENTION

In operating theaters and other medical treatment rooms, many medical appliances and instruments are often used simultaneously or one after another. A medical equipment carrier, in particular a medical equipment trolley, i.e. a medical equipment carrier that can be moved on wheels, may allow a large number of medical appliances and instruments to be arranged in an economically and ergonomically favorable and flexible way.

A medical equipment trolley or another medical equipment carrier is intended not only to be robust and to allow easy cleaning and sterilization, but also to be able to be modified or changed (in particular extended) with little effort and to be able to be assembled safely and correctly, as far as possible even by persons without technical training.

SUMMARY OF THE INVENTION

It is an object of the present invention to make available an improved equipment carrier, in particular an equipment carrier that can be correctly assembled even by personnel not technically trained.

This object is achieved by the subjects of the independent claims.

Developments are set forth in the dependent claims.

An equipment carrier comprises a surface module with a first securing device and a column module with a second securing device, wherein the first securing device on the surface module and the second securing device on the column module are designed corresponding to each other such that the column module and the surface module can be connected to each other with a first, linear movement and a subsequent second, rotational movement of the column module relative to the surface module.

The equipment carrier is in particular a medical equipment carrier, in particular a medical equipment trolley, or an equipment trolley for medical appliances, or an equipment trolley for non-medical uses, or an equipment carrier for stationary medical or non-medical uses, in this connection. The equipment carrier is designed in particular for carrying, making available or storing several medical or non-medical appliances and instruments in an operating theater or another medical treatment room, or in or outside another room. For this purpose, one or more surfaces are provided in particular on the surface module or on additional shelves, on which surfaces it is possible to place medical appliances and instruments or another payload. Moreover, the equipment carrier can have one or more drawers, or compartments that can be closed by doors or flaps.

The surface module is in particular a base module which closes the equipment carrier at the bottom and on which one or more column modules can be arranged, and on the underside of which rollers can be provided. The base module can in particular be rectangular or almost rectangular. Alternatively, the surface module is a bridge module, which connects the column modules not at their lower ends, but at their upper ends or at another location. The surface module, in particular the bridge module, is preferably trapezoidal or approximately trapezoidal. The one or more column modules are in particular elongate and orthogonal to the surface module and, in the intended arrangement of the equipment carrier, are oriented vertically on a horizontal base. With provision of a base module and a bridge module, it is possible for one or more column modules to be arranged vertically on both surface modules and between these. One or more of the column modules can in particular have one or more cavities or channels for receiving cables, connecting lines and the like for attachment to the appliances carried by the equipment carrier.

The first, linear movement, which is needed firstly for connecting the column module to the surface module, takes place in particular vertically or orthogonally with respect to the base module and in particular parallel to the column module. The first, linear movement is a linear movement as far as the position of the column module relative to the surface module in which the second, rotational movement can be performed in order to connect column module and surface module to each other. The first, linear movement ends when the mutually facing top surfaces of the surface module and of the end of the column module facing toward the surface module touch. The connection takes place in particular between a lateral end face of an elongate column module and the surface module.

The subsequent second, rotational movement of the column module takes place in particular about an axis that is parallel to the longitudinal axis of the column module, orthogonal to the base module and vertical in the intended arrangement of the equipment carrier on a horizontal base. The second, rotational movement comprises in particular a rotation about a predefined angle which lies, for example, in the range of between 10 degrees and 120 degrees, in particular in the range of between 20 degrees and 60 degrees. After the first, linear movement has initially been performed, and thereafter the second, rotational movement, the column module is connected at least loosely to the surface module, i.e. the connection does not yet have to be as rigid and firm as is required for the use of the equipment carrier. A firm and rigid connection of the column module to the surface module may additionally require, for example, the tightening of one or more screws.

The combination of pushing and turning, or of a first, linear movement and a second, rotational movement, for an at least loose connection of the column module to the surface module, can represent a simplification particularly for persons without technical training. The first, linear movement and the second, rotational movement can be performed quickly and can simplify the subsequent handling of the two modules connected at least loosely to each other.

The second, rotational movement is in particular a purely rotational movement, which is not associated, as in the case of a screw connection for example, with a further linear movement.

In an equipment carrier as described here, the first securing device comprises in particular one or more securing openings on the surface module, and the second securing device comprises one or more heads on the column module, which heads protrude from the end of the column module facing toward the surface module and are provided and designed for the purpose of engaging in a respective securing opening on the surface module.

In an equipment carrier as described here, the second securing device comprises in particular one or more securing openings on the column module, wherein the first securing device comprises one or more heads on the surface module, which heads protrude from the side of the surface module facing toward the column module and are provided and designed for the purpose of engaging in a respective securing opening on the column module.

The one or more heads are in particular mushroom-shaped or substantially mushroom-shaped or, at least in a plane orthogonal to their movement in the second, rotational movement of the column module relative to the surface module, have a T-shaped or L-shaped cross section or a substantially T-shaped or L-shaped cross section. In planes orthogonal to the direction of the first, linear movement and orthogonal to the rotation axis of the second, rotational movement, the one or more heads have, in particular near the module on which they are secured, a smaller or narrower cross section than they do at a greater distance from this module. The one or more heads each have in particular a shape similar to the head and part of the stem of a screw, which is only screwed in so far that not only the complete head protrudes but also a part of the stem.

In an equipment carrier as described here, the first securing device comprises in particular one or more securing openings on the surface module, wherein the second securing device comprises one or more screws on the column module, and the screw head of the screw or the screw heads of the screws protrude from the end of the column module facing toward the surface module and are provided and designed for the purpose of engaging in a respective securing opening on the surface module.

In an equipment carrier as described here, the first securing device comprises in particular one or more screws on the surface module, wherein the second securing device comprises one or more securing openings on the column module, and the screw head of the screw or the screw heads of the screws protrude from the surface module and are provided and designed for the purpose of engaging in a respective securing opening on the column module.

In an equipment carrier as described here, the one or more securing openings are each designed in particular in the shape of a keyhole.

Like an early type of keyhole for a mortise key, the one or more securing openings have in particular a wide portion and a narrow portion. The wide portion of the securing opening is designed in particular such that the head of a screw or another securing device corresponding to the securing opening can be guided with the first, linear movement through the wide portion. The narrow portion of the securing opening is designed in particular such that the head of a screw or another securing device corresponding to the securing opening can be moved with the second, rotational movement into the narrow portion of the securing opening but cannot there be withdrawn from the securing opening.

The wide portion of a keyhole-shaped securing opening is in particular circular. The narrow portion of a keyhole-shaped securing opening has in particular the form of a strip of constant width in the shape of an arc of a circle, wherein the end of the narrow portion facing away from the wide portion of the securing opening has a semicircular shape, for example. The center of curvature of the arc-shaped strip or the center point of the arc, which is defined by the narrow portion, lies in particular on the rotation axis of the second, rotational movement. In the case of several keyhole-shaped securing openings, the centers of curvature of the narrow portions of all the securing openings lie in particular on the rotation axis of the second, rotational movement. In the case of equal distances from the rotation axis of the second, rotational movement, the narrow portions of all the keyhole-shaped securing openings lie on the same circle or on parallel circles of equal radii, of which the center points lie on the rotation axis. In the case of different distances from the rotation axis of the second, rotational movement, the narrow portions of all the keyhole-shaped securing openings lie on different circles (in the same planes or in several parallel planes) with different radii, of which the center points lie on the rotation axis.

In an equipment carrier as described here, the securing devices are designed and arranged in particular such that the first, linear movement is possible only in a predetermined arrangement and orientation of the column module relative to the surface module.

The securing devices are in particular arranged asymmetrically, in order to permit the linear movement only in a predetermined arrangement and orientation. For example, three screws or heads and three corresponding securing openings are arranged not in the form of an equilateral triangle, but like the corners of a triangle with two or three different side lengths.

An equipment carrier as described here also comprises in particular a further column module, which can be connected to the surface module in the same way as the column module.

In particular, however, the second, rotational movement takes place in opposite directions of rotation in the column module and in the further column module. Especially if, as is described below, both column modules can be connected to each other by a further surface module, the connection of the column modules to the further surface module can at the same time lock the connection of the column modules to the surface module.

An equipment carrier as described here also comprises in particular a further surface module which can be connected to the column modules, wherein the column modules and the further surface module are designed in such a way that the further surface module can be connected to the column modules only when the column modules are positioned and oriented relative to each other as in the case of their intended connection to the surface module.

The further surface module is in particular a bridge module, which interconnects the column modules at their ends which are spaced apart from the surface module and which, in the intended arrangement of the equipment carrier, are at the same time the upper ends. Alternatively, the further surface module is a base module in the sense described above, and the surface module is a bridge module in the sense described above.

On the further surface module, and on the ends of the column modules facing toward the further surface module, corresponding securing devices are in particular arranged in such a way that the connection between the further surface module and the column modules is possible only in the intended relative positioning and orientation of the two column modules. In this way, the connections between the column modules and the surface module are locked when the further surface module is connected to the two column modules. Thus, according to the invention, the column modules are first connected to the surface module, before the further surface module can then be connected to the one or more column modules.

In an equipment carrier as described here, bores are inparticular so arranged on the ends of the column modules facing toward the further surface module, and securing openings are so arranged on the further surface module, that the bores can be brought into coincidence with the securing openings only when the column modules are positioned and oriented relative to each other as in the case of their intended connection to the surface module.

In this case, the further surface module is connected to the column modules in particular by means of screws and/or rivets and/or dowels and/or pins, which are passed right through the securing openings and engage in the bores.

In an equipment carrier as described here, the first securing device comprises in particular a securing opening on the surface module, the second securing device comprises a pull rod on the column module, the pull rod comprises a head, at the end of the column module facing toward the surface module, and a thread, at the end of the column module facing toward the further surface module, the head of the pull rod is provided and designed for the purpose of protruding from the end of the column module facing toward the surface module and of engaging in a securing opening on the surface module, and the thread of the pull rod is provided and designed for the purpose of protruding from the end of the column module facing toward the further surface module and of engaging in a securing opening on the further surface module.

The second securing device can comprise several pull rods on the column module and/or can comprise one or more pull rods in each of several column modules. The thread on the end of the pull rod facing toward the further surface module is in particular an outer thread. The one or more securing openings on the surface module are in particular each keyhole-shaped or substantially keyhole-shaped. By means of a suitable and in particular asymmetrical arrangement of several pull rods and of the corresponding securing openings, it may once again be ensured that each column module can be connected to the surface module and to the further surface module only in an intended relative orientation.

Instead of the thread, each pull rod can have another mechanism for introducing a tensile force, for example a circumferential groove in which a retainer ring, a shank-fastening ring or a locking washer can be inserted or engaged after the end of the pull rod facing toward the further surface module has been guided through.

In an equipment carrier as described here, the securing opening on the further surface module is arranged in particular in such a way that the thread on the pull rod can be inserted into a securing opening in the further surface module only when the column modules are positioned and oriented relative to each other as in the case of their intended connection to the surface module.

In an equipment carrier as described here, the second securing device comprises in particular several pull rods on the column module, wherein the securing openings on the further surface module are arranged in such a way that the threads on all the pull rods can be simultaneously inserted into a respective securing opening in the further surface module only when the column modules are positioned and oriented relative to each other as in the case of their intended connection to the surface module.

The thread on the pull rod or the threads on the pull rods can in particular each be guided partially through the securing openings on the further surface module, such that, when the further surface module bears on the surface modules, they protrude from this further surface module.

In an equipment carrier as described here, in particular by screwing and tightening a screw nut on the thread of the pull rod, the column module assigned to the pull rod can be rigidly connected simultaneously to the surface module and to the further surface module.

An equipment carrier as described here moreover comprises, in particular, recesses in the further surface module for receiving a respective end of a respective column module facing toward the further surface module, wherein the recesses are arranged and designed in such a way that the ends of the column modules facing toward the further surface module can be inserted simultaneously into a respective associated recess only when the column modules are positioned and oriented relative to each other as in the case of their intended connection to the surface module.

The relative arrangement and orientation of the column modules, which is defined unambiguously by the form fit between the ends of the column modules and the recesses, can lock the connection between the column modules and the surface module. The cross sections of the recesses and the corresponding cross sections of the ends of the column modules engaging in the recesses are in particular asymmetrical, for example they do not have a purely circular or elliptical shape or the shape of a regular polyhedron, so as to allow the ends of the column modules to be inserted into the respective recesses only in an intended orientation.

An equipment carrier as described here moreover comprises, in particular, wheels for conveying the weight of the equipment carrier into a floor on which the equipment carrier is standing, wherein the wheels permit low-friction movement of the equipment carrier on the floor.

An equipment carrier as described here moreover comprises, in particular, wheels for conveying the weight of the equipment carrier into one or more rails on which the equipment carrier is standing, wherein the wheels permit low-friction movement of the equipment carrier on the floor.

The wheels are arranged in particular on the surface module or on the further surface module. The wheels and their rotation axles are in particular pivotable in each case about a horizontal axis, so as to permit a movement of the equipment carrier not only in a rectilinear direction. With the wheels, the equipment carrier becomes an equipment trolley.

BRIEF DESCRIPTION OF THE DRAWINGS

Embodiments are explained in more detail below with reference to the attached figures.

DETAILED DESCRIPTION OF THE INVENTION

Figure 1:
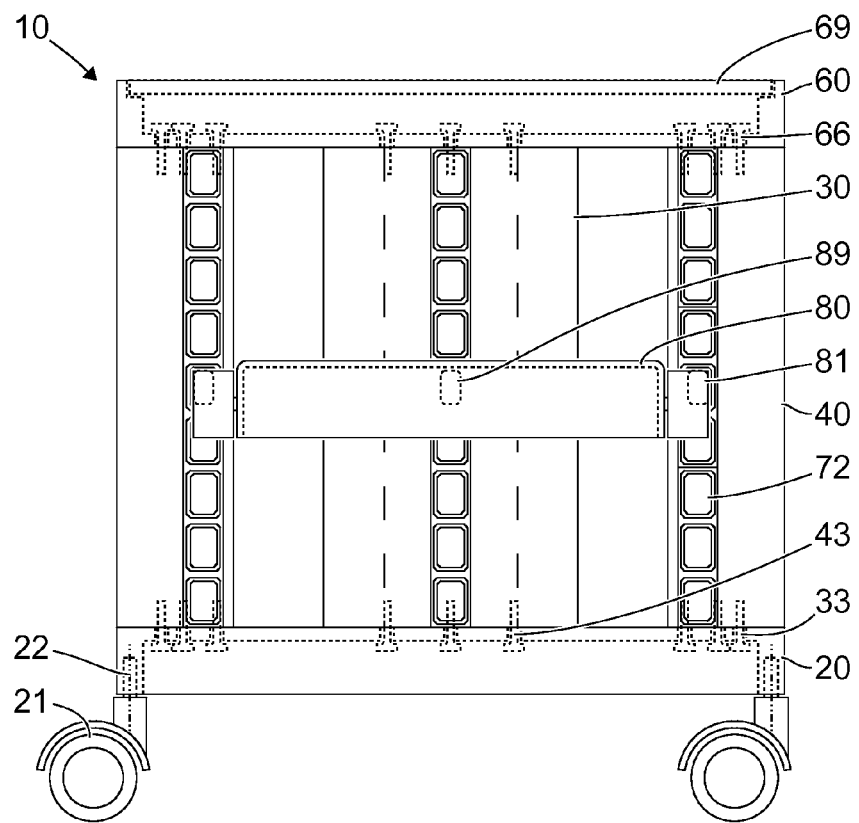
FIG. 1 shows a schematic view of a medical equipment trolley.

FIG. 1 shows a schematic view of a medical equipment carrier, in particular a medical equipment trolley 10. The drawing plane of FIG. 1 is vertical or, in the intended use of the medical equipment trolley 10, orthogonal to a horizontal floor surface on which the medical equipment trolley 10 is standing.

The medical equipment trolley 10 comprises several surface modules, namely a base module 20, a bridge module 60 and a shelf 80, and also several column modules 30, 40. The surface modules 20, 60, 80 extend substantially parallel to the floor surface on which the medical equipment trolley 10 is standing and therefore orthogonally to the drawing plane of FIG. 1. The column modules 30, 40 extend substantially orthogonally with respect to the surface modules 20, 60, 80 and parallel to the drawing plane of FIG. 1.

In the intended use of the medical equipment trolley 10, the base module 20 is arranged at the bottom. A roller unit 21 is arranged on the underside of the substantially rectangular base module 20, at each corner of the base module 20. Each roller unit 21 comprises in particular two rollers, in any case at least one roller, and is pivotable about a vertical pivot axis 22, such that the medical equipment trolley can be pushed and rotated in any desired directions with low friction. In the example shown, the bridge module 60 forms the upper end of the medical equipment trolley 10.

The medical equipment trolley 10 has a front face, which is intended to be directed toward medical personnel and which, in the view in FIG. 1, is directed toward the observer. The rear face of the medical equipment trolley lies opposite the front face and, in the view in FIG. 1, is directed away from the observer. From the direction of the front face, the shelf 80 can be inserted into the medical equipment trolley 10, and, from the direction of the front face, access can be made to medical appliances or instruments placed or mounted or stored on or in the medical equipment carrier 10.

A first column module 30 is arranged centrally on the rear face of the medical equipment trolley 10. The second column modules 40 are arranged symmetrically with respect to each other on the sides of the medical equipment trolley 10, near the front face of the medical equipment trolley 10. Each column module 30, 40 has a plurality of openings 72. The openings 72 are arranged on each column module 30, 40 in a regular grid pattern and are each open in the direction of the front face of the medical equipment trolley 10.

The shelf 80 has one or more pins 89 and two or more engagement hooks 81, which are designed facing the openings 72 and are intended to engage in a respective opening 72. Accordingly, the one or more pins 89 and the engagement hooks 81 in the view in FIG. 1 are directed away from the observer and are concealed by other parts of the shelf 80, for which reason they are only indicated in FIG. 1 by a broken-line contour. The one or more pins 89 are arranged centrally or near the center on the rear edge of the shelf 80 so as to engage in a respective opening 72 in the first column module 30. In a departure from the view in FIG. 1, the first column module 30 can have two or more vertical rows of openings 72. The engagement hooks 81 are provided, arranged and designed to engage in a respective opening 72 in the laterally arranged second column modules 40.

The shelf 80 can be arranged at different heights or at different distances from the base module 20 and from the bridge module 60. On one or both of the engagement hooks 81 and/or on the pin 89, devices (not shown in FIG. 1) are provided for locking the shelf 80 on the column modules 30, 40, which are not shown in FIG. 1. In particular, one or both engagement hooks 81 and/or the pin 89 are each locked in an opening 72, such that the shelf 80 is prevented from accidentally coming loose from its intended position and then falling down.

The column modules 30, 40 are connected rigidly but releasably to the base module 20 by means of screws 33, 43 and to the bridge module 60 by means of screws 66. The screws 33, 43, 66 are not visible from the outside and are therefore indicated in FIG. 1 by broken lines. The inner contours of the cross sections of the base module 20 and of the bridge module 60 are also indicated in FIG. 1 by broken lines. In the example shown, the screws 33, 43 between the base module 20 and the column modules 30, 40 are accessible from the direction of the underside of the medical equipment trolley 10, and the screws 66 between the bridge module 60 and the column modules 30, 40 are concealed by way of a service lid 69.

The medical equipment trolley 10 is easy to assemble and dismantle, especially also by persons without technical training. Moreover, the medical equipment trolley 10 can be modified by exchanging the column modules 30, 40 and/or by exchanging the base module 20 and/or by exchanging the bridge module 60. Moreover, the shelf 80 can be replaced or supplemented by one or more modules with drawers and/or open compartments or compartments closable with flaps or doors and/or by further shelves 80. In the configuration shown, medical appliances, medical instruments and/or other payload can be arranged in particular on the base module 20 and on the shelf 80 and optionally also on the bridge module 60.

Figure 2:
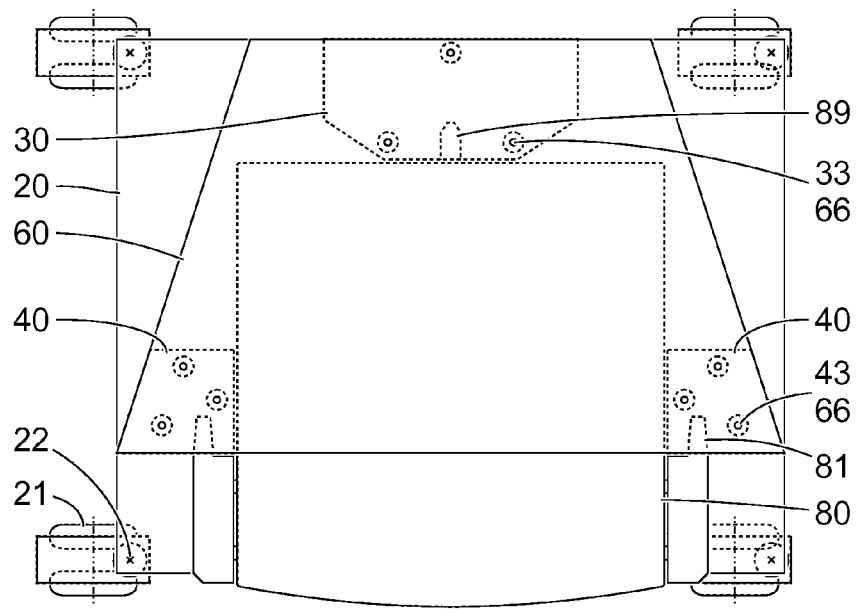
FIG. 2 shows a further schematic view of the medical equipment trolley from FIG. 1.

FIG. 2 shows a further schematic view of the medical equipment trolley 10 from FIG. 1. FIG. 2 shows a plan view, i.e. the drawing plane of FIG. 2 is horizontal or parallel to a floor surface on which the medical equipment trolley 10 stands in its intended arrangement, and therefore orthogonal to the drawing plane of FIG. 1. The rear face of the medical equipment trolley 10 facing away from the observer in the view in FIG. 1 lies at the top in FIG. 2, and the front face of the medical equipment trolley 10 facing toward the observer in the view in FIG. 1 lies at the bottom in the view in FIG. 2.

The rectangular basic shape of the base module 20 with four roller units 21 at the corners can be seen in FIG. 2. The vertical pivot axes 22 of the roller units 21 are orthogonal to the drawing plane of FIG. 2.

Above the base module 20, the column modules 30, 40 extend substantially orthogonally with respect to the drawing plane of FIG. 2. Each column module 30, 40 has a substantially polygonal cross section. The first column module 30 is arranged centrally on the rear face of the medical equipment trolley. The second column modules 40 are designed symmetrically to each other and are arranged symmetrically to each other on the sides of the medical equipment trolley 10. In the example shown, the second column modules 40 are arranged closer to the front face than to the rear face of the medical equipment trolley 10. In the viewing direction of FIG. 2, the column modules 30, 40 are concealed by the bridge module 60. For this reason, only the outer contours of the cross sections of the column modules 30, 40 are indicated by broken lines in FIG. 2.

In the example shown, the bridge module 60 has a substantially trapezoidal basic shape and, in the viewing direction of FIG. 2, conceals part of the shelf 80, which is therefore indicated only by broken lines. The service lid 69 (cf. FIG. 1) and corresponding contours on the top of the bridge module 60 are not shown.

The shelf 80 has engagement hooks 81 which are arranged symmetrically to each other on both sides and which engage in corresponding openings 72 (cf. FIG. 1) in the second column modules 40. Moreover, the shelf 80 has a pin 89, which engages in a corresponding opening 72 (cf. FIG. 1) in the first column module 30.

The screws 33, 43, 66 for connecting the column modules 30, 40 to the base module 20 and to the bridge module 60 are also indicated by broken lines in FIG. 2. In the example shown, the screws 33, 43 for connecting the base module 20 to the column modules 30, 40 on the one hand and the screw 66 for connecting the bridge module 60 to the column modules 30, 40 on the other hand are each arranged exactly vertically over each other in pairs and are therefore congruent in the viewing direction of FIG. 2. Such an arrangement of the screws 33, 43, 66 can be advantageous, for example, when the column modules 30, 40 are designed as extruded profiles having continuous channels. In this case, the screws 33, 43, 66 are in particular screwed into the ends of the channels.

Figure 3:
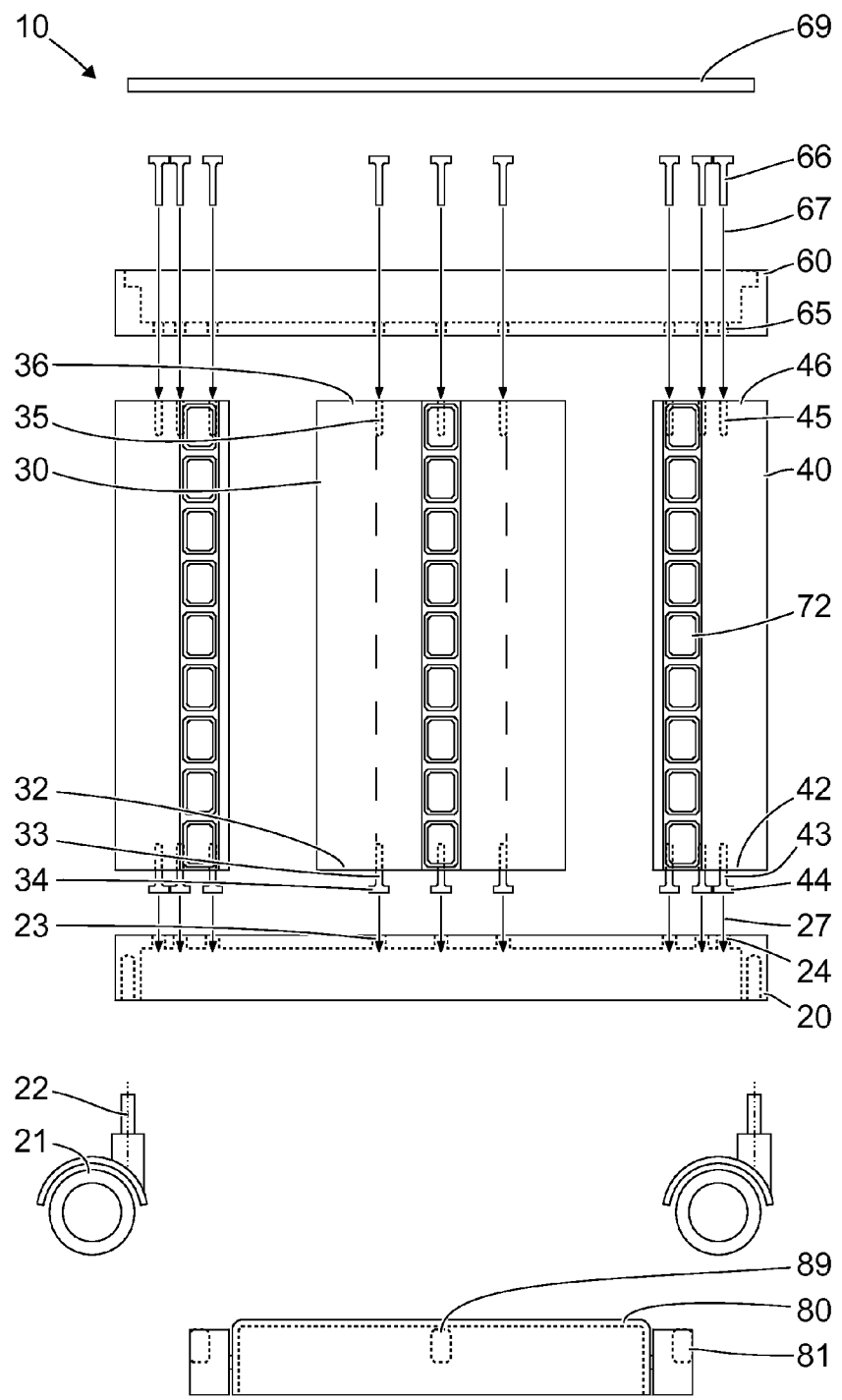
FIG. 3 shows a further schematic view of the medical equipment trolley from FIG. 1.

FIG. 3 shows a further schematic view of the medical equipment trolley 10 from FIGS. 1 and 2. The orientation of the drawing plane corresponds to that of FIG. 1. In contrast to FIG. 1, FIG. 3 shows the component parts of the medical equipment trolley 10 spaced apart from each other in the manner of an exploded view, but in the intended relative orientation.

The medical equipment trolley 10 can be dismantled in particular into the modules or module groups indicated in FIG. 3 and so transported to a hospital or delivered to a medical practice. The roller units 21 can be inserted on the underside of the base module 20, for example in the manner known from office chairs.

The screws 33, 43 are in particular already at the time of delivery inserted or screwed into corresponding bores at the ends 32, 42 of the column modules 30, 40 facing toward the base module 20. The protrusion of the heads 34, 44 of the screws 33, 43 from the ends 32, 42 of the column modules 30, 40 facing toward the base module 20 is in this case adapted to the wall thickness of the base module 20 in the area around securing openings 23, 24 provided for the screws 33, 43.

As is described below with reference to FIG. 4, the securing openings 23, 24 each have in particular the shape of a keyhole. With a first, linear movement 27 of the associated column module 30, 40, each head 34, 44 of a screw 33, 43 can be guided through a correspondingly wide portion of the associated securing opening 23, 24. In a subsequent second, rotational movement described below with reference to FIG. 5, each screw 33, 43 is moved into a narrow area of the associated securing opening 23, 24. In this way, form-fit connections are produced between the screws 33, 43, or their heads 34, 44, and therefore the ends 32, 42 of the column modules 30, 40 facing toward the base module 20, on the one hand, and the base module 20, on the other hand.

To simplify the production of this connection, a certain play can be provided, such that each connection is not yet completely rigid. Thereafter, by tightening the screws 33, 43 from the direction of the underside of the base module 20, the connections between the base module 20 on the one hand and the column modules 30, 40 on the other hand can be completed.

Before or after the tightening of the screws 33, 43 between the base module 20 and the column modules 30, 40, the bridge module 60 can be connected by screws 66 to the opposite ends of the column modules 30, 40. The arrangement of securing openings 65 in the bridge module 60, through which securing openings 65 the screws 66 are guided during insertion 67, and of corresponding bores 35, 45 at the ends 36, 46 of the column modules 30, 40 facing toward the bridge module 60, into which bores 35, 45 the screws 66 are screwed, ensures that the bridge module 60 can be connected to the column modules 30, 40 only when the column modules 30, 40 are correctly connected to the base module 20.

Figure 4:
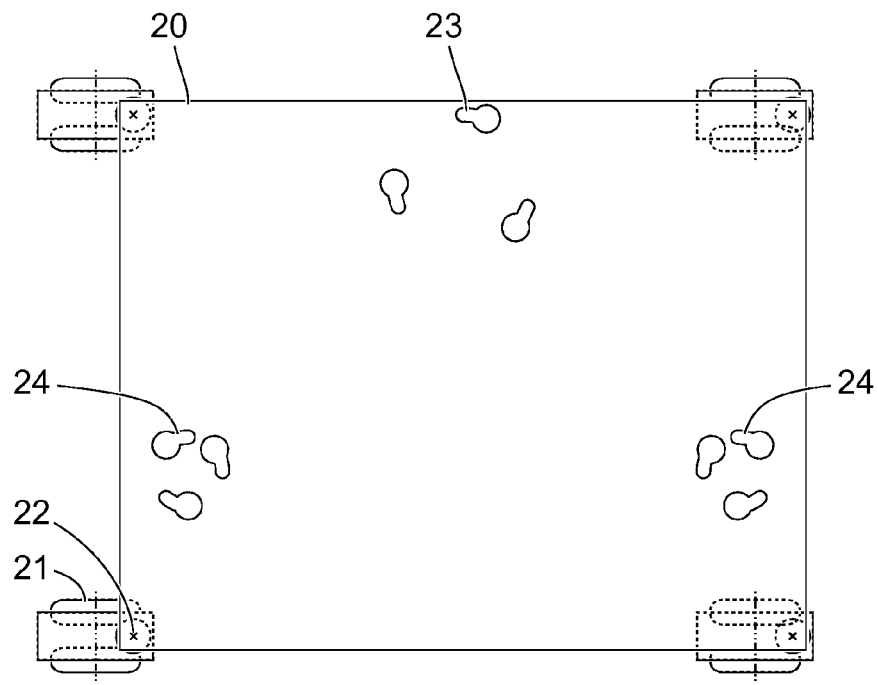
FIG. 4 shows a schematic view of a base module of the medical equipment trolley from FIGS. 1 to 3.

FIG. 4 shows a schematic view of the base module 20 of the medical equipment trolley described with reference to FIGS. 1 to 3. The orientation of the drawing plane of FIG. 4 corresponds to that of FIG. 2.

The keyhole-shaped securing openings 23, 24 in the base module 20 can be seen in FIG. 4. Each securing opening 23, 24 has a wide area, which is designed such that the head 34, 44 of the associated screw 33, 43 can be guided through during the first, linear movement 27 (cf. FIG. 3). Each securing opening 23, 24 in the base module 20 moreover has a narrow area, which is in particular narrower than the head 34, 44 of the respective screw 33, 43, such that a form-fit connection is present as soon as the screw 33, 43 lies in the narrow area of the associated securing opening 23, 24.

Figure 5:
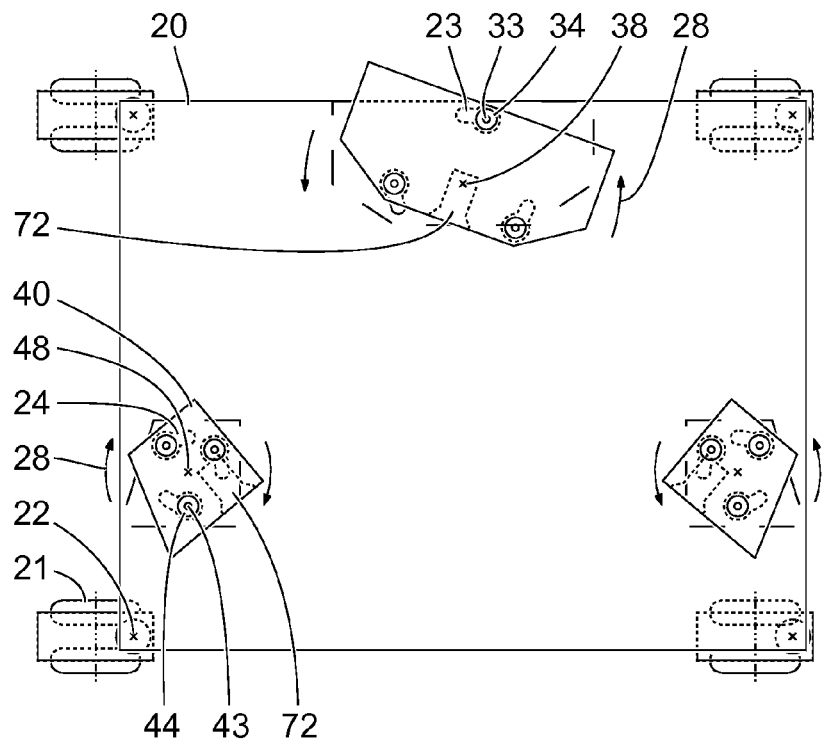
FIG. 5 shows a schematic view of the base module from FIG. 4 and of several column modules.

FIG. 5 shows a further schematic view of the base module 20 and of the column modules 30, 40. The nature of the view, in particular the orientation of the drawing plane, corresponds to that of FIGS. 2 and 4.

In FIG. 5, the screws 33, 43 are shown by quite small circles indicating the cross sections of their shanks, and the heads 34, 44 of the screws 33, 43 are shown by slightly larger circles. The screws 33, 43 are arranged on the ends 32, 42 of the column modules 30, 40 (cf. FIG. 3) directed away from the observer, i.e. facing toward the base module 20, and are therefore concealed by the column modules 30, 40. However, in FIG. 5, the screws 33, 43 are not indicated by broken circles but instead by solid circles, in order to clearly distinguish them from the securing openings 23, 24 in the base module 20.

In FIG. 5, the column modules 30, 40 are oriented relative to each other and relative to the base module 20 in the manner required for inserting the heads 34, 44 of the screws 33, 43 through the securing openings 23, 24 in the first, linear movement 27 (cf. FIG. 3). Accordingly, the heads 34, 44 of the screws 33, 43 on the column modules 30, 40 are in coincidence with the wide areas of the keyhole-shaped securing openings 23, 24 in the base module 20.

For each column module 30, 40, arrows 28 indicate a second, rotational movement, i.e. a rotation about an associated rotation axis 38, 48, with which movement the column module 30, 40 can be brought to the intended position indicated in FIG. 2 among others and indicated in FIG. 5 by widely spaced broken-line contours.

Figure 6:
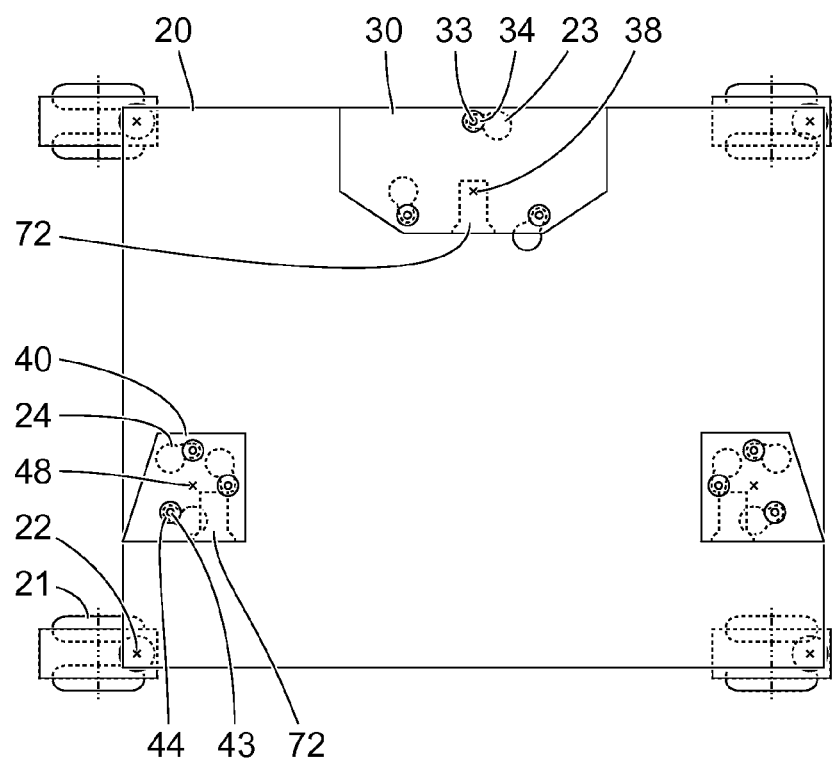
FIG. 6 shows a further schematic view of part of the base module and of the column modules from FIG. 5.

FIG. 6 shows a further schematic view of the base module 20 and of the column modules 30, 40 from FIG. 5. The nature of the view, in particular the orientation of the drawing plane and the view of the screws 33, 43 and of their heads 34, 44, corresponds to that of FIG. 5.

In FIG. 6, the column modules 30, 40 are shown in the intended orientation relative to each other, and relative to the base module 20, reached after the second, rotational movement 28 (cf. FIG. 5). The screws 33, 43 engage through the narrow areas of the keyhole-shaped securing openings 23, 24, such that the column modules 30, 40 are connected with a form fit to the base module 20.

Figure 7:
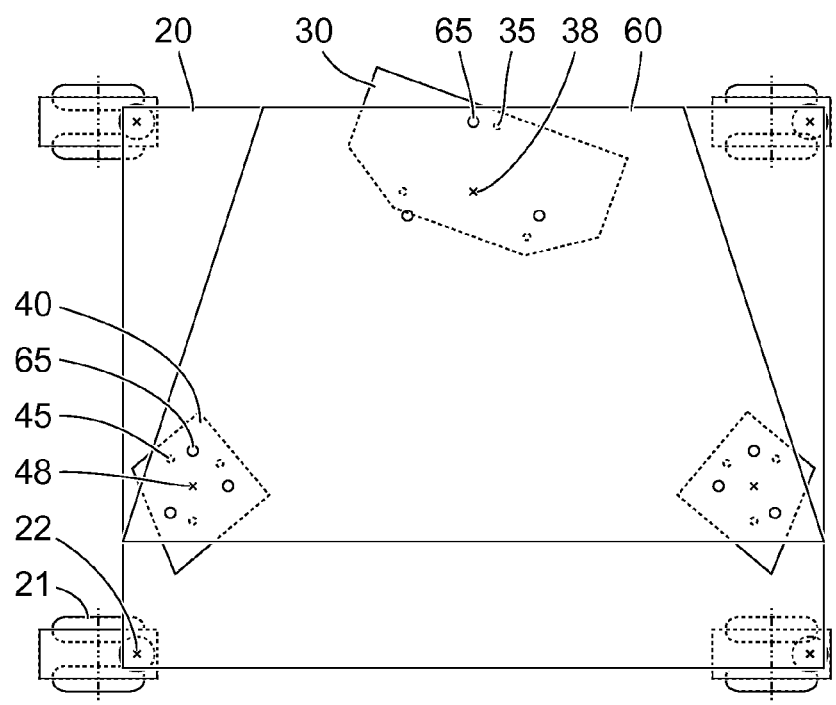
FIG. 7 shows a further schematic view of the medical equipment trolley from FIGS. 1 to 3.

FIG. 7 shows a further schematic view of the base module 20, the column modules 30, 40 and the bridge module 60. The nature of the view in FIG. 7, in particular the orientation of the drawing plane, corresponds to that of FIGS. 2 and 4 to 6. In the same way as in FIG. 2, the service lid 69 (cf. FIG. 1) and corresponding contours on the top of the bridge module 60 are not shown.

In FIG. 7, the column modules 30, 40 are not shown in the intended and final orientation shown in FIG. 6, but again in the orientation shown in FIG. 5. Bores 35, 45 at the ends 36, 46 of the column modules 30, 40 (cf. FIG. 3) facing toward the bridge module 60 are not located in coincidence with securing openings 65 in the bridge module 60. For this reason, the bridge module 60 cannot be connected to the column modules 30, 40 by screws 66 (cf. FIG. 3).

Figure 8:
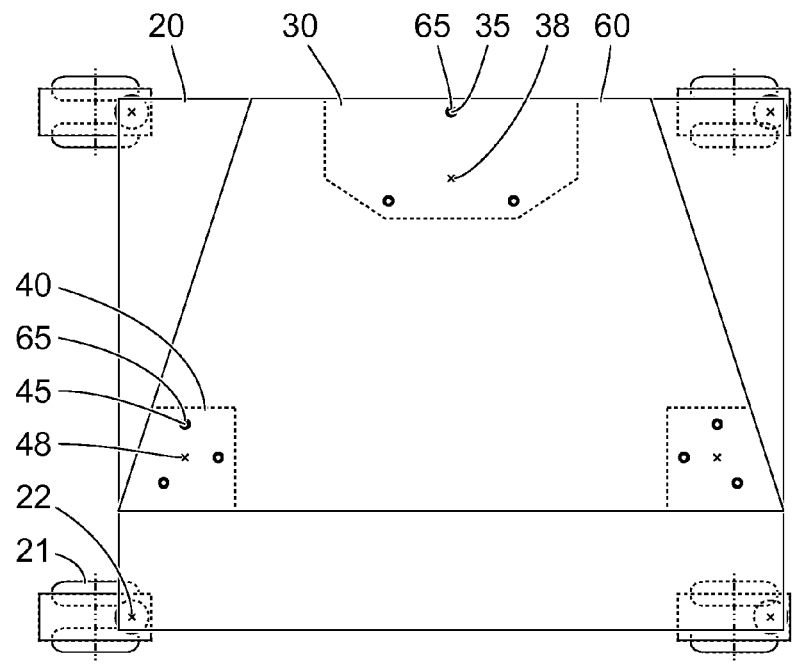
FIG. 8 shows a further schematic view of the medical equipment trolley from FIGS. 1 to 3 and 7.

FIG. 8 shows a further schematic view of the base module 20, the column modules 30, 40 and the bridge module 60 from FIG. 7. The nature of the view, in particular the orientation of the drawing plane, corresponds to that of FIGS. 2 and 4 to 7. In the same way as in FIGS. 2 and 7, the service lid 69 (cf. FIG. 1) and corresponding contours on the top of the bridge module 60 are not shown.

In FIG. 8, the column modules 30, 40 are shown in the intended and final orientation relative to each other and to the base module, which orientation is reached after the second, rotational movement 28 (cf. FIG. 5). Bores 35, 45 at the ends 36, 46 (cf. FIG. 3) of the column modules 30, 40 facing toward the bridge module 60 are in coincidence with securing openings 65 in the bridge module 60. Screws 66 (cf. FIG. 3) can be inserted through the securing openings 65 in the bridge module 60 into the bores 35, 45 in the column modules 30, 40, in order to rigidly connect the bridge module 60 to the column modules 30, 40.

The assembling of the medical equipment trolley can therefore be completed only when the column modules 30, 40, after the second, rotational movement 28 (cf. FIG. 5), have reached the intended orientation in which they are connected with a form fit to the base module 20.

Figure 9:
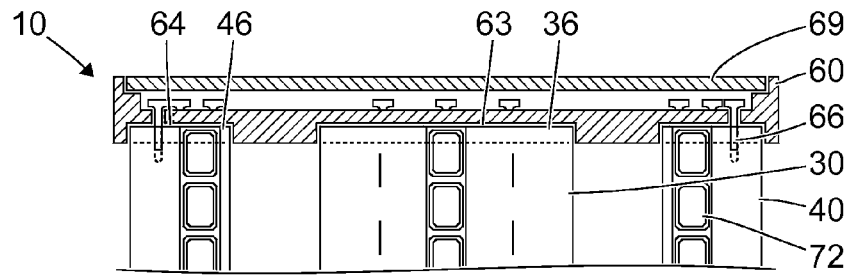
FIG. 9 shows a schematic cross-sectional view of part of a further medical equipment trolley.

FIG. 9 shows a schematic view of part of a further medical equipment trolley which, in terms of some features, properties and functions, is similar to the medical equipment trolley described with reference to FIGS. 1 to 8. Below, features and properties are described in terms of which the medical equipment trolley shown in FIG. 9 differs from the medical equipment trolley described with reference to FIGS. 1 to 8. The orientation of the drawing plane of FIG. 9 corresponds to that of FIGS. 1 and 3. In contrast to FIGS. 1 and 3, the bridge module 60 is shown in FIG. 9 as in a cross section (not along a plane, however, but along a surface that intersects all three column modules 39, 40), in order to reveal recesses in the bridge module 60.

The medical equipment trolley 10 differs in particular from the medical equipment trolley described with reference to FIGS. 1 to 8 in that recesses 63, 64 are provided on the underside of the bridge module 60 facing toward the column modules 30, 40. The position, orientation, size and shape of the first recess 63 in the bridge module 60 correspond to those of the cross section of that end 36 of the first column module 30 facing toward the bridge module. The position, orientation, size and shape of two second recesses 64 arranged symmetrically with respect to each other correspond to those of the cross sections of those ends 46 of the second column modules 40 facing toward the bridge module 60. The second column modules 40 have slightly smaller cross sections than in the medical equipment trolley described with reference to FIGS. 1 to 8. If the bridge module 60 is connected in the intended manner to the column modules 30, 40, the ends 36, 46 facing toward the bridge module 60 engage in the recesses 63, 64 on the underside of the bridge module 60.

Figure 10:
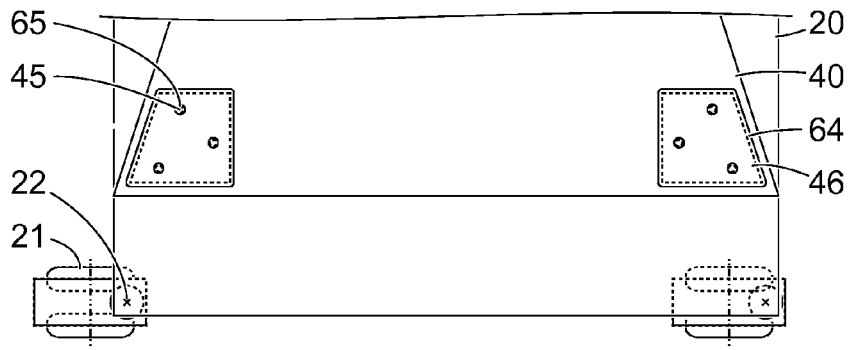
FIG. 10 shows a further schematic view of part of the further medical equipment trolley from FIG. 9.

FIG. 10 shows a further schematic view of part of the medical equipment trolley from FIG. 9. The nature of the view, in particular the orientation of the drawing plane, corresponds to that of FIGS. 2 and 4 to 8. In the same way as in FIGS. 7 and 8, the service lid 69 and corresponding contours on the top of the bridge module 60 are not shown.

In FIG. 10, the contours of the second recesses 64 on the underside of the bridge module 60 are indicated in solid lines, and the outer contours of the ends of the second column modules 40 facing toward the bridge module 60 are indicated in broken lines. The cross sections of the recesses 64 on the underside of the bridge module 60, on the one hand, and of the ends 46 of the column modules 30, 40 facing toward the bridge module 60 correspond to each other completely or substantially. It is thus ensured that the bridge module 60 can be mounted with a form fit onto the column modules 30, 40 only when these have, relative to each other and relative to the base module 20, the intended orientation in which the column modules 30, 40 are connected with a form fit to the base module 60 (cf. FIG. 6 and associated description).

Figure 11:
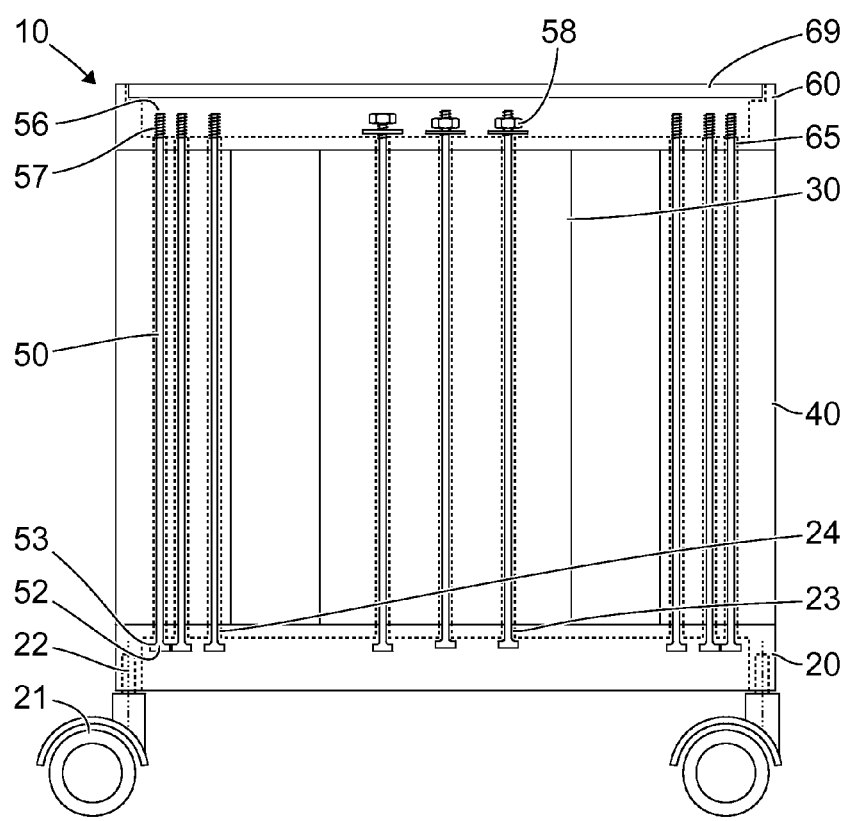
FIG. 11 shows a schematic view of a further medical equipment trolley.

FIG. 11 shows a schematic view of a further medical equipment trolley 10 which, in terms of some features, properties and functions, is similar to the medical equipment trolleys described with reference to FIGS. 1 to 10. The nature of the view, in particular the orientation of the drawing plane, corresponds to that of FIGS. 1 to 9. Below, features and properties are described in terms of which the medical equipment trolley 10 differs from the medical equipment trolley described with reference to FIGS. 1 to 10.

In the medical equipment trolley shown in FIG. 11, securing openings 23, 24 are provided in the base module 20 and securing openings 65 are provided in the bridge module 60, as are described with reference to FIGS. 2 to 8. Instead of the screws 33, 43, 66 that are provided in the medical equipment trolleys described with reference to FIGS. 1 to 10, pull rods 50 are provided in the column modules 30, 40. At its end 52 facing toward the base module 20, each pull rod 50 has a head 53. The head 53 is mushroom-shaped in particular and may be likened to the head of a screw. At its end 56 facing toward the bridge module 60, each pull rod 50 has an outer thread 57. Each pull rod 50 is arranged in the associated column module 30, 40 in an associated channel, which extends from the end 32, 42 facing toward the base module 20 to the end 36, 46 facing toward the bridge module 60. The pull rods 50 can be held in the column modules 30, 40, by measures not shown in FIG. 11, such that they cannot fall out, especially during the transport and assembly of the medical equipment trolley, but are in each case movable in their longitudinal direction within a predetermined range. The heads 53 protrude from the ends 32, 42 of the column modules 30, 40 facing toward the base module 20 in this case, similarly to the heads 34, 44 of the screws 33, 43 in the example described with reference to FIG. 3.

After the column modules 30, 40 have been connected by a first, linear movement 27 (cf. FIG. 3) and then by a second, rotational movement 28 (cf. FIG. 5), the bridge module can be fitted in place when the intended orientation of the column modules 30, 40 has been reached. The ends 56 of the pull rods 50 facing toward the bridge module 60, in particular the threads 57 arranged there, are guided through the securing openings 65 in the bridge module 60 in this case. By applying and tightening screw nuts 58 on the threads 57 on the pull rods 50, the column modules 30, 40 can simultaneously be connected permanently and rigidly to the base module 20 and to the bridge module 60.

REFERENCE SIGNS 10 medical equipment carrier
20 base module (first surface module) of the medical equipment carrier 10
21 roller unit on the base module 20
22 vertical pivot axis of the roller unit 21 (steerability)
23 securing opening (first securing device) in the base module 20 for first column module 30
23 securing opening (first securing device) in the base module 20 for second column module 40
27 first, linear movement of the column module 30 relative to the base module 20
28 second, rotational movement of the column module 30 relative to the base module 20
30 first column module of the medical equipment carrier 10 (behind center)
32 end of the first column module 30 facing toward the base module 20
33 screw (second securing device) on the first column module 30
34 head of the screw 33
35 bore with inner thread on the first column module 30
36 end of the first column module 30 facing toward the bridge module 60
38 rotation axis of the rotational movement 28
40 second column module of the medical equipment carrier 10 (front left, right, arranged with mirror symmetry)
42 end of the second column module 40 facing toward the base module 20
43 screw (second securing device) on the second column module 40
44 head of the screw 43
45 bore with inner thread on the second column module 40
46 end of the second column module 40 facing toward the bridge module 60
48 rotation axis of the rotational movement 28
50 pull rod
52 end of the pull rod 50 facing toward the base module
53 head on the end 52 of the pull rod 50 facing toward the base module 20
56 end of the pull rod 50 facing toward the bridge module
57 thread on the end 56 of the pull rod 50 facing toward the bridge module 60
58 screw nut with thread corresponding to the thread 57 on the pull rod 50
60 bridge module (second surface module)
63 recess in the bridge module 60 for first column module 30
64 recess in the bridge module 60 for second column module 40
65 securing opening in the bridge module 60 for pull rod 50 or for screw 66
66 screw for connection between bridge module 60 and column module 30, 40
67 insertion of the screws 66
69 service lid
72 opening in the column module 30, 40
80 shelf
81 engagement hook on the shelf 80
89 pin on the shelf 80 for engaging in an opening 72

The invention claimed is:

1. An equipment carrier, comprising:
a first surface module with a first securing device and a second securing device;
a second surface module with a first recess and a second recess;
a first column module with a securing device; and
a second column module with a securing device;
wherein the first securing device of the first surface module and the securing device of the first column module correspond to each other such that the first column module and the first surface module connect to each other with a linear movement and a subsequent rotational movement of the first column module relative to the first surface module;
wherein the second securing device of the first surface module and the securing device of the second column module correspond to each other such that the second column module and the first surface module connect to each other with a linear movement and a subsequent rotational movement of the second column module relative to the first surface module;
wherein the first and second recesses permit respective ends of the first and second column modules facing toward the second surface module to simultaneously insert into the respective first and second recesses only when the first and second column modules are connected with the respective first and second securing devices of the first surface module.

2. The equipment carrier according to claim 1, in which the first securing device of the first surface module comprises a securing opening, the securing device of the first column module comprises a screw, and a screw head of the screw protrudes from an end of the first column module facing toward the first surface module and engages in the securing opening of the first surface module.

3. The equipment carrier according to claim 2, in which the securing opening is in the shape of a keyhole.

4. The equipment carrier according to claim 1, in which the first securing device of the first surface module and the securing device of the first column module permit linear movement during connection of the first surface module and the second surface module only in a predetermined arrangement and orientation of the first column module relative to the first surface module.

5. The equipment carrier according to claim 1, in which first and second bores are so arranged on respective ends of the first and second column modules facing toward the second surface module, and the first and second recesses are so arranged on the second surface module, such that the first and second bores are brought into coincidence with the respective first and second recesses only when the first and second column modules are connected with the respective first and second securing devices of the first surface module.

6. The equipment carrier according to claim 5, in which the first securing device of the first surface module comprises a securing opening, the securing device of the first column module comprises a pull rod, the pull rod comprises a head, at an end of the first column module facing toward the first surface module, and a thread, at an end of the first column module facing toward the second surface module, the head of the pull rod protrudes from the end of the first column module facing toward the first surface module and engages in a securing opening of the first surface module, and the thread of the pull rod protrudes from the end of the first column module facing toward the second surface module and engages in a securing opening of the second surface module.

7. The equipment carrier according to claim 6, in which the securing opening of the second surface module is arranged such that the thread of the pull rod is inserted into the securing opening of the second surface module only when the first and second column modules are connected with the respective first and second securing devices of the first surface module.

8. The equipment carrier according to claim 1, further comprising wheels for conveying a weight of the equipment carrier onto a floor on which the equipment carrier is standing, wherein the wheels permit low-friction movement of the equipment carrier on the floor.

* * * * *